(12) United States Patent
Gaskell (10) Patent No.: US 6,845,774 B2
(45) Date of Patent: Jan. 25, 2005

(54) DENTAL DEVICE

(75) Inventor: John Gaskell, Dandenong (AU)

(73) Assignee: MDSA Pty Ltd. (AU)

( * ) Notice: Subject to any disclaimer, the term of this patent is extended or adjusted under 35 U.S.C. 154(b) by 0 days.

(21) Appl. No.: 09/827,262

(22) Filed: Apr. 5, 2001

(65) Prior Publication Data

US 2002/0000230 A1 Jan. 3, 2002

(30) Foreign Application Priority Data

Apr. 7, 2000 (AU) .............................................. PQ6768

(51) Int. Cl.$^7$ ................................................ A61F 5/56
(52) U.S. Cl. ........................ 128/848; 128/859; 602/902
(58) Field of Search ................................ 128/846, 848, 128/859–862; 602/902

(56) References Cited

U.S. PATENT DOCUMENTS

| | | | |
|---|---|---|---|
| 5,427,117 A | | 6/1995 | Thornton |
| 5,566,683 A | | 10/1996 | Thornton |
| 5,829,441 A | * | 11/1998 | Kidd .......................... 128/848 |
| 6,055,986 A | * | 5/2000 | Meade ........................ 602/902 |
| 6,305,376 B1 | * | 10/2001 | Thornton .................... 128/859 |

FOREIGN PATENT DOCUMENTS

| | | |
|---|---|---|
| WO | WO 95/08969 | 4/1995 |
| WO | WO 95/33418 | 12/1995 |
| WO | WO 98/46177 | 10/1998 |
| WO | WO 00/15283 | 3/2000 |

* cited by examiner

Primary Examiner—Michael A. Brown
(74) Attorney, Agent, or Firm—Dinsmore & Shohl LLP

(57) ABSTRACT

A dental device is described in the form of a mandibular splint having two arch members interconnected together by a fastener. The fastener of the present invention includes a flange for locating the fastener in the correct location, two tabs arranged to extend in opposite directions from opposite sides of the body of the fastener for connection to two substantially arcuate wings which are pivotally connected to the fastener. The wings are adjustable in orientation both with respect to each other and with respect to the fastener and are adjustable in length. The fastener is also provided with an adjustable hook or similar arrangement for interconnecting the two arches together in use to maintain the jaws of a person suffering from a sleep disorder at a predetermined spaced apart relationship to open the breathing passages to ameliorate the sleep disorder. Opening of the breathing passages reduces the chances of a person snoring as well as treating other sleep disorders. The fastener may be adjusted by the use when in situ in the mouth of the person using the splint and is continuously adjustable over the duration of the treatment. One form of the adjustable fastener is a set screw arrangement.

34 Claims, 3 Drawing Sheets

DENTAL DEVICE

The present invention relates generally to medical devices, and particularly to dental devices. More particularly, the present invention relates to dental devices for insertion into the mouth of a person suffering from one or more forms of a sleep disorder so as to prevent the incidence of snoring and/or to provide improved breathing during sleep thereby treating the sleep disorder. Even more particularly, the present invention relates to mandibular splints and in particular to an improved adjustable fastener of the type suitable for use with mandibular splints. Even more particularly, the present invention relates to a fastener for connecting the two parts of a two piece mandibular splint together so as to maintain the two parts in contact with each other in such a manner that at least a part of the two pieces are maintained at a predetermined spaced apart interval with respect to each other when inserted into the mouth of a patient suffering from the sleep disorder whilst the patient is asleep. Furthermore, in addition to having an adjustable fastener located between the two parts of the splint each of the two pieces of the splint themselves are adjustable and can be moved to each adopt a number of different orientations in use go as to conform exactly to the anatomy of the mouth of the person wearing the splint such as for example by being aligned with the exact shape of the row of teeth which makes the splint more comfortable to use.

Although the present invention will be described with particular reference to one form of the fastener and one form or the dental device having the fastener it is to be noted that the scope of the present invention is not limited to the described embodiments but rather the scope of the present invention is more extensive so as to include other arrangements and forms of the dental device including the fastener a the two pieces of the splint and the use of the various forms of the device in other applications.

Many people suffer from snoring and its effects. Whilst about 8% of the population, in Australia, suffer from some form of seriously debilitating sleep disorder up to about 20% of the population have a snoring problem of some sort that adversely affects their health. Similar numbers of people in other countries also suffer from some sort form of sleep disorder. The adverse effects of snoring not only affect the snorer but also affect those within earshot of the snorer. Previous attempts to provide devices for preventing snoring or improving breathing during sleep have not been entirely successful for a variety of reasons.

One problem associated with existing anti-snoring devices, such as mandibular splints, is that they are not adjustable and are of the "one size fits all" type which are not adaptable to the specific requirements of the individual having to use the device. In this type of mandibular splint which comprises an upper arch connected to a lower arch by a suitable connector, the relative positions of the upper and lower arches with respect to each other cannot be adjusted. The connector by which the lower jaw is extended forward is not adjustable by the user thereby resulting in possible discomfort whilst using the splint as well as the splint being ineffective in treating the sleep disorder.

Another problem of this type of splint is there is no flexibility in the actual shape that the upper and lower arches of the device can adopt in order to conform to the bite of a person wearing the splint or adjustability in the size of the wings forming the arches of the device to accommodate different sized bites and mouths. In such devices the orientation of the wings of the arch members is constant, as is the length of the wings. In many instances such devices cannot be used or if used are uncomfortable because they cannot be adjusted to fit the user's mouth.

Another type of mandibular splint is of the fully customized variety which requires fitting by a skilled person such an a dentist or an advanced dental technician or similar and/or requires custom manufacture of the device in a factory or laboratory both of which add considerably to the cost of the device. In the past the cost of having a fully customised device fitted by a dentist could be in excess of many hundreds of or even thousands of dollars. Also, during treatment it was not possible to change the shape or orientation of the splint since it was not adjustable. Any adjustment that was necessary required manufacture of a new splint.

Thus, existing devices suffer from one or more problems of not being adjustable or being inflexible in not being adaptable to the anatomy of the mouth of a person, particularly the orientation and/or curvature of the teeth and gums ie. the bite, and not being adjustable in length of the wings to take into account the differently shaped anatomy of the mouths of different individuals, or being extremely expensive if a fully tailor made or customized device is provided, which in not usually adjustable. Therefore, there is a need to provide a dental device in the form of a mandibular splint that can be used to reduce or eliminate snoring and provide improved breathing during sleep which is readily adjustable and can be readily fitted to the exact requirements of an individual at a inexpensive or reasonable cost thereby providing a wider range of individuals with the opportunity of treatment for sleep disorders.

Thus, it is an aim of the present invention to provide a dental device which will reduce or eliminate snoring and/or provide improved breathing during sleep which in comfortable to use by being tailor made or customised to each individual's requirements by being adjustable in both orientation and size and being available at a low cost.

According to the present invention there is provided a fastener adapted for use with a mandibular splint for treating a person suffering from sleep disorder said fastener including:

a locating means for locating the fastener at a preselected position for forming a first arch member of the mandibular splint particularly for positioning the arch member in the mouth of the person being treated;

a connecting mean for connecting the first arch member to a second arch member of the mandibular splint in use of the splint, said connecting means being adjustable to selectively adjust the position Of the first and second arch members with respect to each other to a predetermined position, and an attachment means for use in attaching an extension meter to the first member for forming at least a part of the first arch member wherein, the extension member is selectively movable about the attachment means to adapt a selective orientation in accordance with the specific requirements of a person being treated for the sleep disorder.

According to another aspect of the present invention there is provided an arch member of a mandibular splint for treating a person Suffering from sleep disorder, said arch member including a fastener and at least one extension member wherein;

the fastener has a locating means for locating the fastener for forming the arch member;

a connecting means for connecting the arch member to another arch member, said connecting means being adjustable so as to selectively adjust the position of the two arch members with respect to each other; and an attachment means for attaching the extension member to the fastener for forming the arch member wherein, the extension member is selectively movable about the attachment means to adopt a selective orientation with respect to the fastener to form the arch member in accordance with the specific requirements of a person being treated for the sleep disorder.

According to another aspect of the present invention there is provided a mandibular splint for treating a person suffering from sleep disorder, said splint including;

two arch members connected together in use of the splint wherein, at least one of the arch members includes a fastener and at lease one extension member wherein, said fastener includes a locating means for locating the fastener when forming the arch member;

a connecting means for connecting the two arch members together in use of the splint;

said connecting means being adjustable to selectively position the two arch members with respect to each other in a predetermined position; and an attachment means for attaching at least one extension member to the fastener wherein, the extension member is selectively movable about the attachment means to adopt a selected orientation with respect to the fastener in accordance with the specific requirements of a person being treated for the sleep disorder and wherein, said other arch member is provided with a connection means complementary to the connection means of the first arch member so as to maintain the two arch members in the predetermined spatial arrangement.

According to a still further aspect of the present invention there is provided a method of treating a person suffering from sleep disorder with a mandibular splint including:

two arch members where at least one arch member is provided with an adjustable fastener for connection the two arch member together;

said method including the steps of either sequentially or simultaneously locating the to arch members either in combination or separately in the oral cavity of the person, connecting the two arch members together if required, and selectively adjusting the position of the two arch members with respect to each other by adjusting the adjustable fastener wherein, the adjustable fastener provided on one of the arch members includes;

a locating means for locating the fastener;

a connecting means for connecting the two arch members together; and an attachment means for attaching at least one extension member to the fastener wherein, the extension member in selectively movable about the attachment means to adopt a selective orientation with respect to the fastener in accordance with the specific requirement of the person being treated.

Typically the fastener is made up of a number of different components in which one of the components is a base plate and another is a cover. More typically all of the components are made from stainless steel. Even more typically, the components are hand worked and vibration polished to remove all sharp edges.

Typically the locating means is a flange, tag, tab, flap, loop, ring, groove, aperture, or the like. More typically the locating means extends substantially perpendicularly from the base plate to assist in locating the fastener within the mouth. Even more typically, the flange, etc. is located centrally within the fastener, and is located at or towards the front of the arch member. Typically, the flange, etc. abuts against part of the mouth in use Typically the connecting means is a hook, clip, clasp, post, projection or similar. More typically, the hook, etc is movable with respect to the base plate and/or cover. Even more typically the shank of the hook is provided with an internally threaded aperture for receiving an externally threaded shaft or similar so that rotation of the shaft within the aperture moves the hook with respect to the base plate and/or cover. More typically the hook is part of a set-screw of similar adjustment mechanism.

Typically, part of the cover is spaced apart from the base plate then the base plate and cover are assembled together, so as to form a cavity, cage, enclosed space or similar. More typically, the hook is located intermediate the base plate and the cover. Even more typically, the cover is provided with a slot through which a part of the hook, preferably the shank is received. More typically, the shank of the took moves in the lengthwise extending direction of the slot.

Typically the attachment means is a flap, tab, tag or similar extending outwardly from the base plate. More typically the tab, etc. is provided with an aperture. Even more typically there are two connecting means extending in opposite directions from opposed sides of the base plate. More typically, the tabs, etc. are angularly inclined to the base plate. Even more typically, the tabs, etc. are in stepped relationship with the base plate.

Typically the extension member is a wing, more typically a substantially arcuate shaped wing, and even more typically an arcuate wing of adjustable length. Typically the wing is provided with a boss, stud or similar projection at or towards one and, preferably the proximal end. Even more typically the projection is received within the aperture of the tab allowing pivotal movement of the wing with respect to the fastener about the base, etc. Even more typically, there are two wings extending in opposite directions from the opposed flaps or tabs of the base plate. Both wings are independently movable of each other to align with the teeth ion either side of the mouth.

Typically the wing or wings are continuously selectively positionable between limits to adopt a variety of orientations with respect to the fastener. More typically the orientation of the wings can extend from subtending an angle of about 13° to 41° between the wings. A typical range of orientations adopted by the wings are 13°, 27° and 41° of inclination between the two wings. Even more typically the outer edges of the distal portions of the two wings can be spaced apart in the range from being greater than about 86 mm to being less than about 64 mm.

Typically the wings extending on either side of the fastener include a tray member and a deformable thermoplastic material or the like located within the tray member. More typically the arch member of the present invention is symmetrical about its central axis. Alternatively, the arch member can be asymmetrical about the centre line of the arch member. The deformable thermoplastic material is provided within which an impression of the teeth of the person using the splint is produced by holding the material when in a softer state against the teeth for a sufficient period of time to form the impression.

Typically, the complementary form of the connecting means includes a lip, shelf, groove, slot, flange or similar. More typically, the lip, etc faces rearwardly or is rearwardly directed and is located at or towards the centre of the arch member. Even more typically, the hook, etc. is provided on one arch member and the lip, etc. is provided on another arch member. More typically, the tip, etc. of the hook of the connecting means on one arch member engages with the lip, etc. on the other arch member so that movement of the hook causes corresponding movement of the arch member having the lip, etc. to bring the lower jaw forward with respect to the upper jaw thereby altering the shape of the airway to reduce or prevent snoring and/or to treat the sleep disorder.

Typically, the fastener is manually adjustable using a special tool such as an allen key or hexagonal shaft or the adjustment is motorised such as, for example, by using a diode motor or microvolt motor to automatically extend the lower jaw forward by adjusting the position of one arch member with respect to another arch member. More typically, the adjustment is continuously variable or is step wise variable.

The present invention will now be described by way of example with reference to the accompanying drawings in which.

Figure 2:
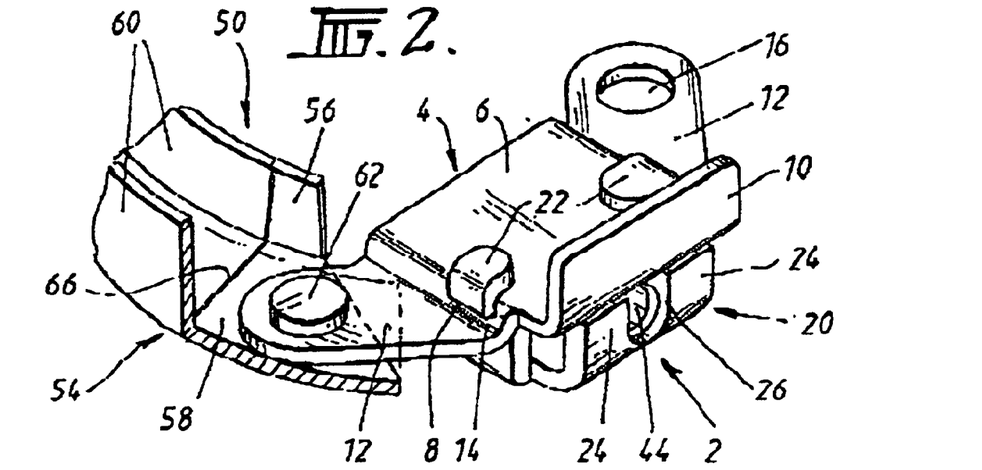
FIG. 2 is a partial top perspective view of one form of the fastener of the present invention attached to one wing to form part of one arch member.
Figure 3:
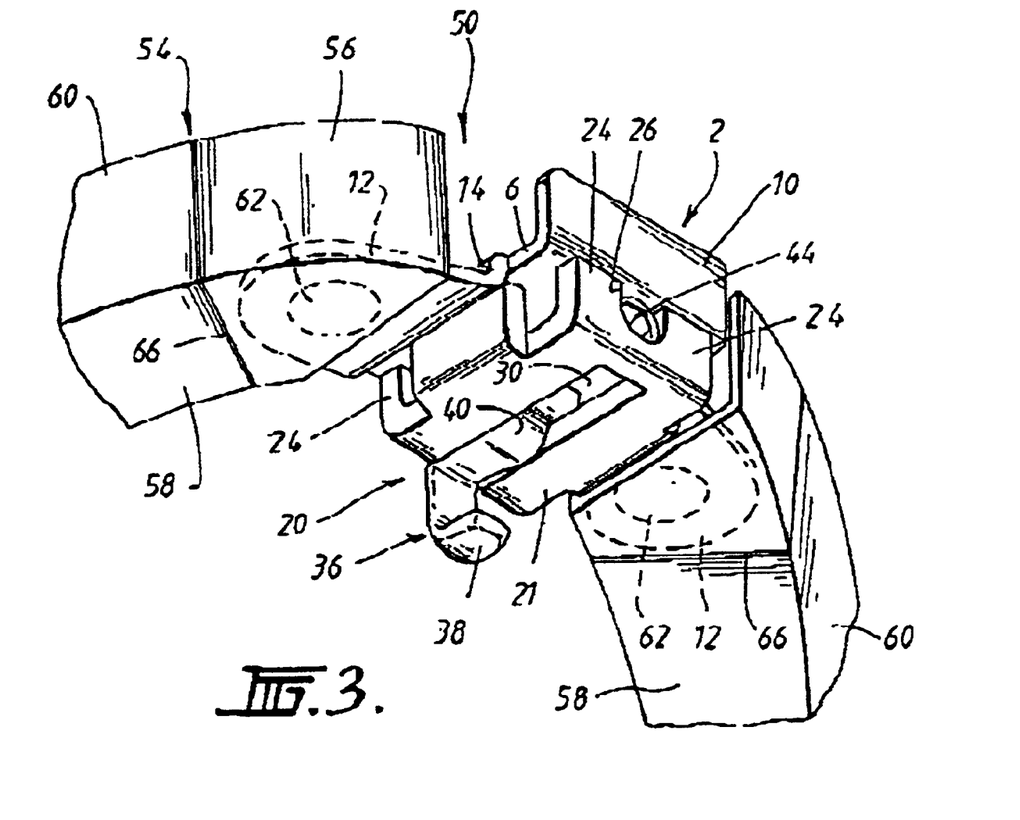
FIG. 3 is an underneath perspective view of the fastener showing the fastener attached to two wings forming one of the arches of the present invention.
Figure 4:
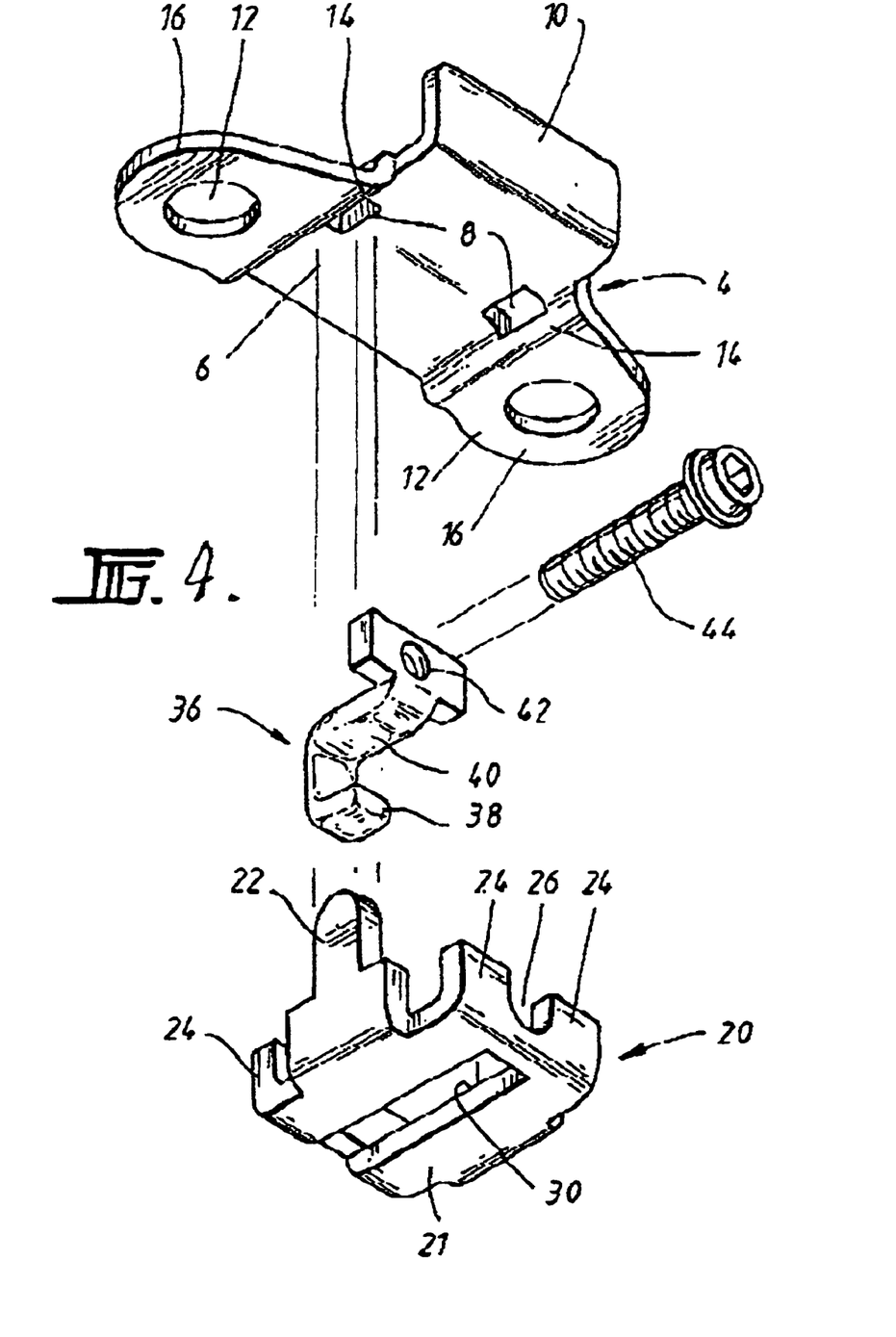
FIG. 4 is an exploded isometric view of the components of the fastener of the present invention.

With particular reference to FIGS. 2, 3 and 4, one form of the fastener of the present invention will be described. The fastener which is generally denoted by reference number 2 is in the form of a generally double winged set screw that comprises four individual components as is shown more particularly in exploded form in FIG. 4. The first of the components is a stainless steel base plate, generally denoted as 4, which has been hand worked and vibration polished to remove all sharp edges, burrs or the like. Base plate 4 includes a centrally located generally square or rectilinear planar body portion 6 which is provided with a pair of opposed square cut-outs or apertures 8 at or towards opposite side edges of the body portion.

A locating means in the form of a flange 10 is provided along one side edge of body portion 6 of the base plate 4, generally intermediate of the location of square apertures 8. Flange 10 assists in locating the fastener in the mouth in the correct position and assists in locating the fastener in the correct position. A pair of substantially planar opposed tabs or tags 12 extend outwardly from opposed sides of body portion 6. It is to be noted that the pair of tabs 12 extend from the sides of body portion 6 having apertures 8. Each of the tabs 12 is provided with a shoulder 14 along the edge adjacent to the side edge of body portion 6 to move the level of tab 12 from being in the plane of body portion 6 into being in a stepped relationship with the body 6. Optionally, tab 12 may extend in the same plane as body portion 6 or may be inclined to the body portion 6 so as to be angularly inclined to body portion 6 rather than being in a stepped relationship. Each tab 12 in provided with a circular aperture 16. Tabs 12 form part of the attachment means for attaching the extension members or wings of the arches of the present invention to fastener 2 as will be described in more detail later.

A stainless steel cover 20 which has also been hand worked and vibration polished to remove all sharp edges, burrs or the like is located in intimate contact with base plate 4 a shown more particularly in FIGS. 2 and 3. Cover 20 comprises a body portion 21 and a pair of outwardly depending projections in the form of prongs, tangs, tabs or similar generally denoted as 22. In use in forming fastener 2 prongs 22 are received in respective square apertures 8 and are bent, folded or twisted so as to securely retain cover 20 in place on base 4 with a cavity chamber, space or the like being formed between the base plate and cover.

Figures 1, 5A, 5B:
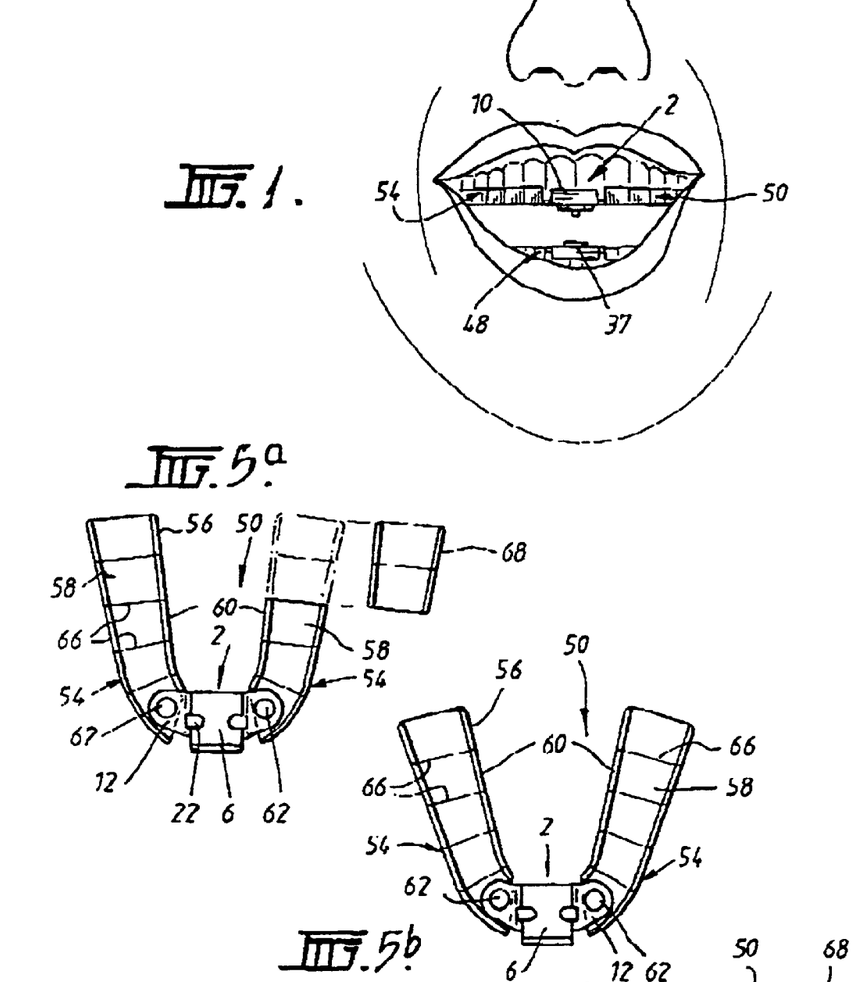
FIG. 1 is a front view of one form of a mandibular splint having the fastener of the present located in situ in the mouth of a person using the splint but with the upper and lower arches not yet connected together.
FIG. 5a is a top plan view of the upper arch have a fastener when in one orientation in which the wings are relatively closer together and showing two segments of the wing separated from the upper arch.
FIG. 5b is a view similar to FIG. 5a in which the wings are located in an intermediate position with respect to each other and are intact.

Cover 20 in also provided with flanged portions in the form of spacers or posts 24 located at regularly spaced apart locations around the periphery of the body 21 of cover 20 in order to space body portion 21 from body portion 6 of base plate 4 go as to define the cavity, chamber or similar therebetween. An aperture 26 is located between two adjacent spacers 24 along one edge of the body portion 21 of cover 20 to allow access into the cavity defined between the cover and base plate. Aperture 26 and posts 24 are located on the same side as flange 10. Body portion 21 is provided with slot 30. In use, aperture 26 is accessible through the mouth of the person wearing the mandibular splint as shown in FIG. 1 to allow the splint to be adjusted in situ during use.

A connecting means in the form of a hook 36 in provided with fastener 2. Part of hook 36 is located within the cavity formed intermediate cover 20 and base plate 4 with the distal end or tip 38 of the hook 36 extending beyond cover 20 and shank 40 of hook 36 being received through slot 30. The part of shank 40 located with the cavity is provided with an internally threaded aperture 42 for receiving a threaded allen bolt 44, stud or similar device.

Hook 36 is free to move along the lengthwise extending direction of slot 30 in response to rotation of allen bolt 44. Hook 36 in one form of the connection means of the fastener or the present invention other forms of the connection means are possible. Movement of the position of the hook 36 with respect to cover 20 a base plate 4 provides for adjustment of the two arches forming the mandibular splint as will be described in more detail later in this specification.

With particular reference to FIGS. 2, 3 and 5a to 5c, one form of the arch member of the present invention will be described. This form of the arch member is the upper arch member. It is to be noted that two arch members being a lower arch 48 and an upper arch 50 form the mandibular splint as shown in FIG. 1. The two arch members are interconnected together by hook 36 whereby one of the arch members which is typically the upper arch member 50 has the fastener 2 of the present invention and the other arch member, typically the lower arch member 48, has a complementary connecting means 37 such as for example a receiving means in the form of an edge, flange, loop or the like for receiving the hook. The hook 36 is received in the receiving means to maintain the two arch members 48,50 in their spatial relationship to each other during use of the splint when the two arches 48,50 are connected together.

Figure 5C:
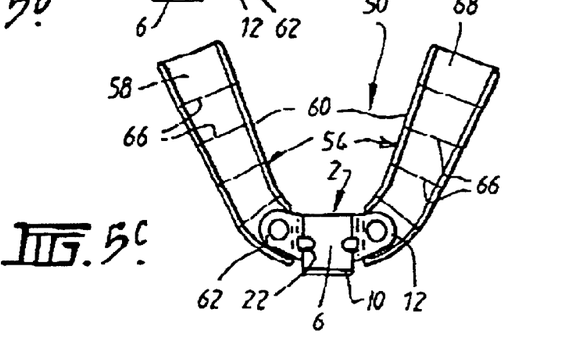
FIG. 5c is a view similar to FIG. 5a in which the wings are located relatively further apart from each other, and are intact.

Arch member 50 includes fastener 2 positioned intermediate two extension members in the form of wings 54 located on either side of the fastener 2. Each wing 54 includes a tray 56 in the form of a floor 58 and two side walls 60 having a boss, stud or similar projection 62 extending from the floor 58 of the tray. Stud 62 is located at or towards proximal end of the tray. The boss or stud 62 is received in circular aperture 16 of tab 12 of fastener 2. Accordingly, wing 54 or tray 56 in free to pivotably move with respect to fastener 2 about aperture 16 to adopt a number of different orientations. A selected number of the different orientations that can be adopted by the wings are shown in FIGS. 5a to 5c in which the two wings 54 are shown as being relatively move closer together in FIG. 5a, being located in an intermediate spaced apart orientation in FIG. 5b, and relatively more spaced apart from each other in FIG. 5c. The position of the wings 54 are determined in accordance with the anatomy, such as the bite, of the person being fitted for the mandibular splint of the present invention so that the splint in both comfortable to wear and provides a clear breathing passage to prevent snoring thereby providing improved breathing during sleep.

With particular reference to FIGS. 5a to 5c, each wing 54 is optionally provided with a number of substantially parallel spaced apart break lines 66 dividing wing 54 or tray 56 into separate segments 68. The break lines 66 are arranged to allow the length of the wing 54 or tray 56 to be selected in accordance with requirements by bending or cutting the wing or tray along the selected break line to sever the segments for removal from the wings and then removing the superfluous distal part of the wing or tray an shown in the right hand side of FIG. 5a.

When the correct orientation of the wings both with respect to fastener 2 and with respect to each other have been determined and when the exact length of the wings has been determined a deformable thermoplastic material in a pliable condition is added to the tray 58 and hardened in order to maintain the arch member in that orientation by making the arch member rigid. It is to be noted that the hardened thermoplastic material traps tab 12 of fastener 2 to tray 56 so as to prevent further pivotal movement of the wing with respect to the fastener.

Tray 56 may be made from any suitable material, such as for example, materials used in making dental devices and in dentistry generally including methylmethacrylate or polycarbonate resins an other thermoplastic materials or thermoset materials.

The deformable material may be of any suitable type which is thermoplastic and which binds to the tray 56. The deformable material is used for custom forming of a mould of the persons teeth, including both the upper and lower teeth to ensure proper fitting of the upper and lower arch members to the upper and lower jaw respectively.

The complementary connecting means or receiving means 37 fitted to the arch member not having fastener 2 can take any number of suitable forms. One form is a lip, shelf, ledge or similar formed centrally in the arch member and facing rearwardly into the mouth cavity. The tip 38 of hook 36 which is forwardly directed or forwardly facing engages around the edge of the inwardly facing lip and contracts the rear edge. When the position of hook 36 relative to base plate 4 and cover 20 is moved, typically in a forward direction, hook tip 38 engages the lip and forces the arch member in a forward direction which in turn forces the lower jaw in a forward direction to increase the opening of the breathing passages thus ameliorating the effects of snoring or sleep disorders.

Alternatively, the complementary connecting means 37 is a receiving means in the form of a groove, slot or similar for receiving the tip 38 of hook 36.

A particularly preferred form of the complementary engaging means 37 is flange 10 of another base plate 4. In this embodiment instead of all of the components of fastener 2 being used to form the arch member, only base plate 4 is used in combination with two wings 54 or trays 56 to form the other arch member ie. base plate 4 is used to interconnect the two wings to form the other arch member. This arch member does not have a fastener but only base plate 4.

In this embodiment flange 10 of base plate 4 is contacted by hook 36 associated with the fastener of the other arch member so that when the position of hook 36 is adjusted, typically in a forward direction, hook tip 38 engages against flange 10 to force the arch member having base plate 4 alone, typically in a forward direction.

Operation of the mandibular splint having the fastener of the present invention will now be described.

An arch member, say arch member 50, is formed either by attaching two trays 56 to opposite sides of fastener 2 or by attaching two wings 54 comprising the trays 56 and deformable material to a centrally located fastener 2. The first arch member 50 provided with fastener 2 is heated to soften the deformable material and the arch member inserted in the mouth, say to contact the upper set of teeth in order to mould the arch to the exact shape of the upper teeth. At this stage the orientation of the wings with respect t the fastener can be determined in accordance with the exact curvature of the teeth or bite of the teeth. Additionally, the length of each wing can be determined in accordance with the bite of the upper teeth by breaking each wing at the appropriate break line 66 and removing any superfluous segments 68 as shown in FIG. 5a. When the exact shape of the upper arch member has been determined the arch member is cooled in order to harden the deformable material to set the shape of the upper arch thereby preventing further deformation or change of shape. At this stage the wings 54 are set and prevented from further movement or rotation.

A second arch member, typically the lower arch member 48, having the complementary connecting or receiving means, say a lip or base plate 4 having flange 10 only connecting the two wings together is placed in the mouth against the lower teeth in an orientation XXX to that of upper arch 50 and conformed to the exact shape of the lower teeth by moulding the arch member. The arch member is removed and cooled to harden it so that it retains in the exact mould shape.

Once both upper and lower arch members 50,48 of the mandibular splint are prepared they are placed separately in the mouth with the hook 36 of the upper arch in contact with the lip or flange 10 of the lower arch. The orientation of fastener 2 is such that aperture 26 is forwardly facing towards the mouth and thus provides easy access to the head of allen bolt 28. A suitable tool, such as an allen key or the like, is inserted into the mouth through aperture 26 to contact the head or alien bolt 44. The tool is rotated to rotate alien bolt 44 which in turn moves the position of hook 36 lengthwise along slot 30. Since hook 36 is in contact with the lip of the lower arch 48, the lower arch is forced forward also. As the lower arch is moulded to lower teeth movement of the lower arch 48 forces the lower jaw forward so that the breathing passages are realigned or opened no that the breathing passage is less restricted thereby preventing snoring and improving breathing during sleep. Further adjustment of the device can be done by the person whilst the device is being worn by the person being treated. The splint can be readily adjusted by the wearer whilst it in located within the mouth, thereby obviating the need for a specialist technician or similar to adjust it. Further, as the treatment progresses further adjustment can be made in situ in accordance with new requirements to improve the success of the treatment.

Advantages of the present invention include the following:

The fastener of the present invention allows a more comfortable mandibular splint to be formed.

The splint has greater flexibility in conforming to a wide range of different mouth anatomies in that greater variations in the degree of curvature of the mouth or bite can be accommodated and conformed to as well as the length of the wings or trays of the arch members can be altered to suit individuals requirements.

The splint can be made at a lower cost because it can be mass produced and then adopted to suit individual's needs.

The fastener can be adjusted at will in situ by the person using the splint as the need arises during use and during the treatment.

The described arrangement has been advanced by explanation and many modifications may be made without departing from the spirit and scope of the invention which includes every novel feature and novel combination of features herein disclosed.

Those skilled in the art will appreciate that the invention described herein is susceptible to variations and modifications other than those specifically described. It in understood that the invention includes all such variations and modifications which fall within the spirit and scope.

What is claimed is:

1. A dental splint comprising: a first arch member comprising a first extension member and a second extension member; and
a fastener that interconnects the first and second extension members to form the first arch member, the fastener including:
a first attachment member for adjustably attaching one of the first or second extension members of the first arch member to the fastener allowing selective angular adjustability of the first extension member to the first attachment member, and;
a second attachment member for adjustably attaching the other of the first or second extension members to the fastener to provide for selective angular adjustability of the second extension member with respect to the second attachment member, wherein the respective positions of the first and second extension members are selectively angularly adjusted with respect to the fastener by hinged or pivotal movement about the respective attachment members to adopt selective orientations within the mouth of the person to accommodate the specific requirements of the person being treated in order to treat the sleep disorder.

2. A dental splint according to claim 1 further comprising a second arch member cooperative with said first arch member through said fastener.

3. A dental splint according to claim 2, further comprising:
a locator for locating the at a preselected position within the mouth of the person being treated; and
an adjustable connector for cooperatively connecting the first arch member to the second arch member for selectively adjusting the position of the first and second arch members with respect to each other to adopt a predetermined position within the mouth of the person being treated.

4. A dental splint according to claim 3 in which the fastener includes a base plate and a cover.

5. A dental splint according to claim 4 in which the locator is located centrally within the fastener and is located at or towards the front of the fastener in use.

6. A dental splint according to claim 5 in which the locator is a flange, tag, tab, loop, ring, groove, post defining an aperture therein, or flap.

7. A dental splint according to claim 4 in which the adjustable connector is movable with respect to at least one of the base plate or cover.

8. A dental splint according to claim 7 in which the adjustable connector includes a hook, clip, or clasp.

9. A dental splint according to claim 8 in which the hook is provided with a shank and the shank is provided with an internally threaded aperture for receiving an externally threaded shaft so that rotation of the shaft within the aperture moves the hook with respect to at least one of the base plate or cover.

10. A dental splint according to claim 9 in which at least part of the hook is located in a cavity or chamber formed intermediate the base plate and the cover.

11. A dental splint according to claim 10 in which the cover is provided with a slot through which a part of the hook is received for movement in a lengthwise extending direction of the slot.

12. A dental splint according to claim 11 in which the part of the hook received for movement in a lengthwise extending direction of the slot is the shank of the hook.

13. A dental splint according to claim 12 in which the attachment member is a flange, flap, tab or tag extending outwardly from the base plate of the fastener.

14. A dental splint according to claim 13 in which the flange or tab is provided with an aperture.

15. A dental splint according to claim 13 in which there are two attachment members in the form of flanges or tabs extending in opposite directions from opposed sides of the base plate.

16. A dental splint according to claim 15 in which the flanges or tabs are angularly inclined to the base plate or are in stepped relationship with the base plate or are in a common plane of the base plate.

17. A dental split according to claim 4 which the locator extends substantially perpendicularly from the base plate.

18. A dental splint according to claim 1 in which the extension member is, or is provided with, a wing.

19. A dental splint according to claim 18 in which the wing is an arcuate shaped wing.

20. A dental splint according to claim 19 in which the arcuate wing is adjustable in length.

21. A dental splint according to claim 18 in which the wing is provided with a frangible section or break-line permitting unwanted segments of the wing to be removed from the wing in order to adjust the length of the wing.

22. A dental splint according to claim 21 in which the wing is provided with a projection in the form of a boss, stud or raised connecting portion located at or towards one end for pivotal connection of the wing to the flange or tab of the fastener allowing pivotal movement of the wing with respect to the base plate.

23. A dental splint according to claim 22 in which the projection is received within an aperture provided in the tab, providing pivotal movement of the wing with respect to the fastener.

24. A dental splint according to claim 23 in which there are two wings extending in opposite directions from the opposed tabs provided on either opposed side of the base plate allowing separate pivotal movement of the wings to conform to the anatomy of the mouth of the person using the device.

25. A dental splint according to claim 24 in which the wing or wings are continuously selectively positionable with respect to the fastener to adopt a variety of orientations in order to accommodate differences in individual requirements depending upon the anatomy of the mouth of the person using the splint.

26. A dental splint according to claim 25 in which the orientation of the wings about the fastener can extend from subtending an angle of about 13° to about 41° between the wings or with respect to the center line of the fastener.

27. A dental splint according to claim 26 in which the wings extend on either side of the fastener include a tray member and a deformable thermoplastic material located within the tray member, such that the material is mouldable when soft to conform to the shape of the teeth of the person using the device.

28. A dental splint according to claim 1 in which the connector engages a complementary connector provided on or in the second arch member, in which the complementary connector is in the form of a lip, shelf, groove, slot, flange, ring or loop.

29. A dental splint according to claim 28 in which the complementary connector is rearwardly directed and is located at or towards the center of the second arch member.

30. A dental splint according to claim 28 in which a hook disposed on the connector engages with a lip or flange of the complementary connector so that movement of the hook causes corresponding movement of the second arch member having the lip or flange to bring the lower jaw forward with respect to the upper jaw thereby altering the shape of the airway to reduce or prevent snoring.

31. A dental splint according to claim 1 which is manually adjustable or is automatically adjustable using either a means for manual adjustment or a means for motorized adjustment.

32. An arch member of a dental splint for use in treating a person suffering from a sleep disorder, the arch member comprising:
   at least one extension member; and
   a fastener comprising:
      a locator for locating the fastener within the mouth of the person being treated;
      an adjustable connector for connecting the arch member to another arch member, the connector being adjustable so as to selectively adjust the position of the two arch members with respect to each other; and
      a hinged attachment member for attaching the extension member to the fastener such that the extension member is selectively movable about the attachment member to adopt a selective orientation with respect to the fastener to form the arch member in accordance with the specific requirements of a person being treated for the sleep disorder.

33. A dental splint for treating a person suffering from a sleep disorder, the splint including two arch members connected together in use of the splint, wherein at least a first of the arch members includes:
   at least one extension member;
   a fastener comprising:
      a locator for locating the fastener when forming the arch member; and
      an adjustable connector for connecting the two arch members together in use of the splint, the connector being adjustable to selectively position the two arch members with respect to each other in a pre-determined position; and
   a hinged attachment member for attaching at least one extension member to the fastener wherein the extension member is selectively movable about the attachment member to adopt a selective orientation with respect to the fastener in accordance with the specific requirements of a person being treated for the sleep disorder,
   wherein the other arch member is provided with a complementary connector which is complementary to the adjustable connector of the first arch member to maintain the two arch members in the pre-determined position.

34. A method of treating a person suffering from sleep disorder with a dental splint, the splint including two arch members where at least one arch member is provided with an adjustable fastener for connecting the two arch members together, the method including the steps of:
   either sequentially or simultaneously locating the two arch members either in combination or separately in the oral cavity of the person;
   connecting the two arch members together, if required; and
   selectively adjusting the position of the two arch members with respect to each other by adjusting the adjustable fastener and a hinged attachment member, wherein the adjustable fastener provided on one of the arch members includes:
      a locator for locating the fastener within the mouth of the person being treated; and
      an adjustable connector for connecting the two arch members together; and
         wherein the attachment member provided on one of the arch members is configured for attaching at least one extension member to the fastener wherein the extension member is selectively movable about the attachment member to adopt a selective orientation with respect to the fastener in accordance with the specific requirement of the person being treated.

* * * * *

UNITED STATES PATENT AND TRADEMARK OFFICE
CERTIFICATE OF CORRECTION

PATENT NO. : 6,845,774 B2
DATED : January 25, 2005
INVENTOR(S) : Gaskell

It is certified that error appears in the above-identified patent and that said Letters Patent is hereby corrected as shown below:

Column 9,
Line 50, "A dental splint according to claim 1 further comprising" should read -- A dental splint according to claim 1, further comprising --; and
Line 55, "a locator for locating the at a preselected position within" should read -- a locator for locating the fastener at a preselected position within --

Signed and Sealed this

Thirty-first Day of May, 2005

JON W. DUDAS
*Director of the United States Patent and Trademark Office*